(12) United States Patent
Pfromm et al.

(10) Patent No.: US 7,700,312 B2
(45) Date of Patent: Apr. 20, 2010

(54) PREPARATION CONTAINING NANOSCALE PARTICLES WITH ELECTROSTATICALLY ADHERED ENZYME

(75) Inventors: Peter Pfromm, Manhattan, KS (US); Kerstin Wuerges, Heusenstamm (DE)

(73) Assignee: Kansas State University Research Foundation, Manhattan, KS (US)

( * ) Notice: Subject to any disclaimer, the term of this patent is extended or adjusted under 35 U.S.C. 154(b) by 548 days.

(21) Appl. No.: 11/301,213

(22) Filed: Dec. 12, 2005

(65) Prior Publication Data

US 2006/0183208 A1 Aug. 17, 2006

Related U.S. Application Data

(60) Provisional application No. 60/636,843, filed on Dec. 16, 2004.

(51) Int. Cl.
*C12P 1/00* (2006.01)
*C12N 11/14* (2006.01)
*C12N 9/00* (2006.01)

(52) U.S. Cl. ............................ 435/41; 435/176; 435/183

(58) Field of Classification Search ........................ None
See application file for complete search history.

(56) References Cited

U.S. PATENT DOCUMENTS

| | | | |
|---|---|---|---|
| 4,258,068 A | 3/1981 | Huffman | |
| 4,304,857 A | 12/1981 | Brouillard et al. | |
| 4,377,597 A | 3/1983 | Shapiro et al. | |
| 5,100,680 A | 3/1992 | Matthews et al. | |
| 5,405,752 A * | 4/1995 | Nilsson | 435/7.94 |
| 5,643,721 A * | 7/1997 | Spring et al. | 435/6 |
| 5,976,527 A * | 11/1999 | Siol et al. | 424/94.1 |
| 6,171,813 B1 | 1/2001 | Dordick et al. | |
| 6,479,146 B1 * | 11/2002 | Caruso et al. | 428/403 |
| 6,696,089 B2 * | 2/2004 | Kabanov et al. | 424/484 |

OTHER PUBLICATIONS

Combinatorial Formulation of Biocatalyst Preparations for Increased Activity in Organic Solvents: Salt Activation of Penicillin Amidase; Lindsay, J.P., Clark, D.S., and Dordick, J.S.; Published online Jan. 14, 2004 in Wiley InterScience/www.InterScience.wiley.com; 2004 Wiley Periodicals, Inc.

Improving Enzymes by Using Them in Organic Solvents; Alexander M. Kilbanov; Nature; vol. 409: Jan. 11, 2001; pp. 241-245.

The Effect of Water on Enzyme Action in Organic Media; Aleksey Zaks and Alexander M. Klibanov; vol. 263, No. 17, Issue of Jun. 15 The Journal of Biological Chemistry; pp. 8017-8021, (1988).

Enzymatic Catalysis in Nonaqueous Solvents; Aleksey Zaks and Alexander M. Klibanov; vol. 263, No. 7, Issue of Mar. 5, 1988; The Journal of Biological Chemistry; pp. 3194-3201.

Enzyme-Catalyzed Processes in Organic Solvents; Aleksey Zaks and Alexander M. Klibanov; Proc. Natl. Acad. Sci. USA, vol. 82, May 1985; Biochemistry, pp. 3192-3196.

Fumed Silica Activated Subtilisin Carlsberg for Catalysis in Hexane: Performance in a Packed Bed Reactor; Wurges, K., Pfromm, P.H., Rezac, M.E., and Czermak, P; Department of Chemical Engineering, Kansas State University, Manhattan, KS; Wurges et al Reactor paper 1 10; Nov. 23, 2005; pp. 1-18; AICHE Meeting, Nov. 2005.

Activation of Subtilisin Carlsberg in Hexane by Lyophilization in the Presence of Fumed Silica; Wurges, K., Pfromm, P.H., Rezac, M.E., and Czermak, P.; Journal of Molecular Catalysis B; Enzymatic 34 (2005) pp. 18-24.

Enzymatic Catalysis in Monophasic Organic Solvents; Jonathan S. Dordick; Enzyme Microb. Technol., 1989, vol. 11, April; pp. 194-211.

Activation of Enzymes in Hexane Using an Inert Support: Fumed Silica; Pfromm, P.H., Rezac, M.E., Czermak, P, Hoffman, Y., and Wurges, K.; Presentation of the Department of Chemical Engineering, Kansas State University, Manhattan, Kansas; AICHE Meeting, Nov. 2005.

* cited by examiner

*Primary Examiner*—David M Naff
(74) *Attorney, Agent, or Firm*—Hovey Williams LLP

(57) ABSTRACT

Improved catalytic enzyme preparations are provided which effectively catalyze reactions carried out in organic solvents. The preparations comprise nanoscale solid support particles (e.g., fumed silica or alumina) having enzyme molecules electrostatically adhered to the surfaces of the particles. The preparations are prepared by mixing together solid support particles and enzyme molecules in an aqueous system under pH conditions establishing opposite charges on the support particles and enzyme molecules, respectively. The water is then removed from the system, preferably by pre-freezing followed by lyophilization to yield free-flowing, particulate catalyst particles which can be used in liquid organic reactions or in packed bed reactors.

7 Claims, 13 Drawing Sheets

PREPARATION CONTAINING NANOSCALE PARTICLES WITH ELECTROSTATICALLY ADHERED ENZYME

RELATED APPLICATION

This application claims the benefit of Application Ser. No. 60/636,843 filed Dec. 16, 2004, and such prior application is incorporated by reference herein.

BACKGROUND OF THE INVENTION

1. Field of the Invention

The present invention is broadly concerned with improved enzyme preparations which are capable of catalyzing a variety of chemical reactions carried out in organic solvents. More particularly, the invention is concerned with such enzyme preparations, methods of preparing the preparations, and use thereof in catalyzed reactions, wherein the enzyme preparations comprise enzyme molecules electrostatically adhered to nanoscale solid particles such as fumed silica or fumed alumina.

2. Description of the Prior Art

So-called "nonaqueous enzymology" has become an important area of research and development. Enzymes exhibit a wide array of novel reactivities and selectivities in non-aqueous solvents. For example, many reactions that are impossible in water due to kinetic or thermodynamic reasons can be performed in organic solvents due to the suppression of water-induced side reactions. Improved and altered substrate specificities and selectivities can be observed. Examples of practical applications are enantioselective synthesis and combinatorial biocatalysis. The possibility of the solubilization of hydrophobic substrates or products in organic solvents opens opportunities for the enzymatic production of poorly water soluble fine chemicals and pharmaceuticals. The thermal and storage stability of enzymes can be significantly enhanced in nonaqueous media.

One challenge for the use of enzymes in organic media is the decreased catalytic activity which is in general orders of magnitude lower compared to aqueous solution. Several methods to overcome this disadvantage have been investigated. Reversed micelles, the immobilization on a variety of materials, or surface modification of the enzyme can be employed. Immobilization on ceramics was reported for the improvement of enzymatic catalysis at low temperatures. Addition of disodium hydrogenphosphate or L-alanine prior to lyophilization was reported to improve enantioselectivity but not the enzyme activity over native lipase for a reaction in isopropylether.

One of the most successful methods to increase the relatively low activity of enzymes in organic media is the addition of inorganic salts before lyophilization of the enzyme. The activity of subtilisin Carlsberg (SC) in different organic solvents was increased almost 4000 fold by addition of 98 wt % of KCl (relative to the final enzyme preparation mass) to the enzyme in aqueous buffer solution prior to lyophilization. At optimum water concentration in the solvent a 27000 fold enhanced activity of SC in hexane compared to the salt-free lyophilized enzyme was reported. (Ru et al., *Biotechnol. Bioeng.* 75 (2001) 187, hereafter "Ru et al.") See also U.S. Pat. No. 6,171,813.

The detailed mechanism of this enzyme activation by freeze-drying in presence of KCl is not entirely clear. It has been hypothesized that the enzyme-bound water (sometimes termed essential water) is the main factor of altered enzyme activity in organic media. This water is thought to provide the enzyme molecule with the internal mobility which is apparently necessary for enzymatic catalysis. By adding highly kosmotropic salts prior to freeze-drying aqueous enzyme solutions this essential water is thought to be supplied to the enzyme via the salt. According to this view, the presence and type of salt would have a significant influence on activation.

However, salt-activation of enzymes for use in organic solvents presents a number of practical difficulties. The preparative procedure is relatively cumbersome, requiring prefreezing in liquid nitrogen to achieve high surface areas for enzyme immobilization. Moreover, no simple particle size control is possible, and it is very difficult to adapt the procedure to pound-scale production owing to the intricate salt crystallization process. Finally, some of the proposed salts and salt mixtures are relatively expensive (e.g., CsCl, on the order of $150.00/pound), and the natural hygroscopicity of salts present storage and fabrication problems.

SUMMARY OF THE INVENTION

The present invention overcomes the problems outlined above and provides greatly improved enzyme preparations useful for catalyzing reactions carried out in organic solvents. Broadly speaking, the enzyme preparations of the invention comprise nanoscale-size solid support particles with enzyme molecules electrostatically adhered to the surfaces of the particles. Such particles may be solid, inorganic, water insoluble materials which do not absorb water to any appreciable degree, such as inorganic oxides, especially fumed silica (FS) and fumed alumina. However, other nanoscale materials may be used so long as particles are solid and capable of electrostatic bonding with enzymes in the aqueous phase. Advantageously, the particles should have a diameter of from about 0.1-100 nm, more preferably from about 10-75 nm, and most preferably from about 20-50 nm. The surface area of the particles should be from about 100-2550 $m^2/g$, more preferably from about 150-500 $m^2/g$, and most preferably from about 175-300 $m^2/g$.

In some instances the solid support particles aggregate into bodies e.g., fumed silica having a primary particle diameter of from about 7-50 nm are linked together by fusion and —OH bonding, forming chain-like aggregates having high specific surface areas on the order of 100-400 $m^2/g$ and lengths of from about 100-1000 nm, more preferably from about 200-300 nm.

A wide variety of enzymes may be used to form the catalytic preparations of the inventions. Exemplary enzymes include those selected from the group consisting of catalytic antibodies, oxidases, oxidoreductases, transferases, lyases, isomerases, ligases, hydrolases with acyl transferase activity in organic solvents, peroxidases, tyrosinases, dehydrogenases, lipases, proteases, nucleases, aldolases, phosphatases, sulfatases, chymotripsins, tannases, subtilisins, papain, pepsin, thermolysin, thrombin and mixtures thereof.

It has been found that best results are obtained when the enzyme is present on the surface of the solid support particles as a monolayer or separated monolayer, with little or no agglomeration or "stacking" of enzyme. In this way, maximum catalytic sites are presented by the enzyme preparations. The solid support particles should have enzyme over an area of up to about 70% of the total surface area thereof.

The enzyme catalysts of the invention can be easily and inexpensively prepared. Generally, the method involves mixing together the solid support particles with enzyme molecules in an aqueous system and under pH conditions establishing opposite charges on the particles and the enzyme molecules respectively. The aqueous system preferably includes from about 1-98% by weight solid particles, more preferably at least 25% by weight; and most preferably at least 50% by weight, based upon the weight of the enzyme in the system. The enzyme molecules are caused to electrostatically adhere to the surfaces of the support particles. Thereupon, water is removed from the system. Preferably, the solid support particles and enzymes have respective isoelectric points, and the pH is adjusted to a level between these isoelectric points. Thus, the enzyme molecules electrostatically adhere to the support particles in the aqueous system prior to water removal.

In preferred practice, the aqueous system containing the enzyme molecules and support particles is sonicated to assure intimate mixing without subjecting the enzyme to excessive shear. Normally, the system is created by first dispersing the enzyme molecules in aqueous dispersant and thereafter adding the support particles. A buffer is also usually added in order to maintain accurate pH control. The water removal step is most preferably carried out via lyophilization, with or without pre-freezing of the aqueous system. Pre-freezing may be accomplished using liquid nitrogen or simple freezer treatment. In any case, the lyophilization is entirely conventional and serves to remove virtually all of the water from the system. The lyophilization may be carried out for about 24-96 hours, more preferably about 36-84 hours at primary drying condenser and constant shelf temperatures within the range of −70° C. to −30° C., more preferably about −60° C. to −40° C., and secondary drying condenser and constant shelf temperatures of from about 0° C. to 40° C., and more preferably about 10° C. to 30° C. Alternatively, the water removal step may be accomplished by passing a drying gas such as nitrogen over the system until drying to a constant weight is accomplished.

The enzyme preparations of the invention can be used in any appropriate enzymatically catalyzed reaction carried out in organic solvent. As used herein "organic solvent" refers to a solvent which is at least predominately organic in character, but some water may also be present. Generally, the organic solvent chosen should not interfere with the desired enzymatic catalysts. Representative organic solvents include toluene, benzene, hexane, cyclohexane, hexadecane, methylene chloride, chloroform, ethyl acetate, butyl acetate, diethyl ether, 2-butanone, dimethylsulfoxide, dioxane, dodecane, hexyl acetate, isopropyl ether, tetrahydrofuran, acetonitrile, carbon tetrachloride, butyl ether, ethyl ether, acetone, dimethylformamide, pyridine, diisopropyl ether, trichloroethylene, methyl-t-butyl ether, benzine, three-pentanone, dichloromethane, vinyl acetate, t-amyl alcohol, heptane, cyclohexane, 2,2,4-trimethylpentane, acetonitrile, 2-methyl-2-butanol, t-butyl acetate, N-methylacetamide, triethylamine, tetrahydrofuran, pyridine, 1-3 acetonitrile, nitrobenzine, acetone, cyclohexanone, butanone, 2-pentanone, 2-hexanone, t-butyl acetate, t-butyl alcohol, supercritical organic solvents, ionic liquids, deep eutectic solvents, and mixtures thereof.

The enzyme preparations hereof are used in lieu of or as partial replacements for conventional enzymatic solvent catalysts. Typical catalyzed reactions may be selected from the group consisting of transesterification, esterification, aminolysis, alcoholysis, acylation, polycondensation, hydrolysis, oxidation, and HCN addition to carbonyl compounds. Other specific examples include enzymatic biodiesel production from renewable oils, the processing of natural and mineral oils, and the production of chiral and other pharmaceuticals.

The enzyme preparations can also be used in packed bed reactors for catalyzing chemical reactions. The preferred preparations are free-flowing powders, and can be readily packed into a reaction column.

Although the inventors do not wish to be bound to any particular theory, it is believed that the low activity of enzymes in organic solvents is primarily due to mass transfer limitations. Since enzymes are not soluble in organic solvents, they will remain in the form of massive "sheets" of protein that form during freeze-drying of pure enzyme from aqueous systems. Accordingly, the invention provides high surface area primary support particles which electrostatically support enzyme molecules in a monolayer or separated monolayer form and which largely overcome the mass transfer problem. Importantly, this is done without the use of salts and their attendant problems.

DETAILED DESCRIPTION OF THE PREFERRED EMBODIMENT

Figure 1:
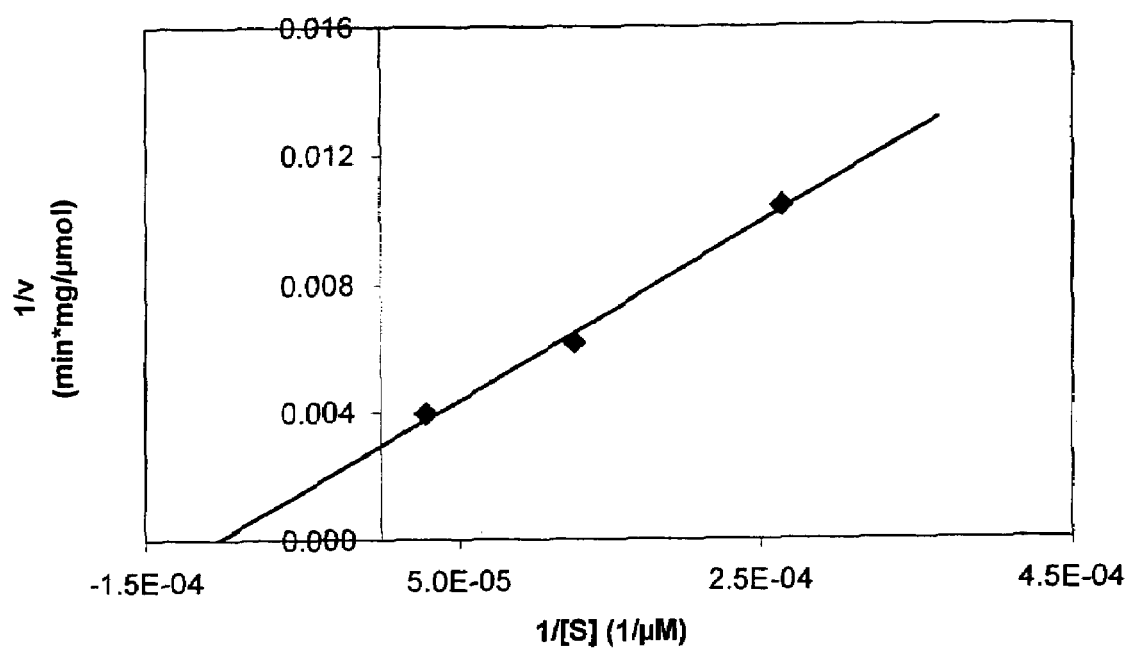
FIG. 1 is a Lineweaver-Burk plot using the reaction rate data derived using the 98.5 wt. % fumed silica/SC preparations described in Example 1.

The following examples set forth preferred procedures for the preparation and use of the activated enzymes of the invention. It is to be understood, however, that these examples are provided by way of illustration and nothing therein should be taken as a limitation upon the overall scope of the invention.

Example 1

The following example describes preferred techniques for the production of activated SC on a fumed silica support, and a determination of the kinetics of the activated SC as compared with conventional enzyme products in a transesterification reaction.

Materials

SC (EC 3.4.21.14; proteinase from *Bacillus licheniformis*; specific activity of 8 units/mg solid), fumed silica (purity of 99.8%, specific surface area of 258 m$^2$/g, particle diameter 7-50 nanometer, as reported by the manufacturer), and nonadecane (puriss. p.a. standard for GC) were obtained from Sigma-Aldrich (St. Louis, Mo.). Aeroxide® Alu C (spec. surface area: 100+/−15 m$^2$/g) was obtained as a sample from Degussa Corporation (Parsippany, N.J.). N-acetyl-L-phenylalanine ethyl ester (APEE, purity>99%) was obtained from Bachem California Inc. (Torrance, Calif.). KH$_2$PO$_4$ (purity>99%), hexane (optima grade, purity>99.9%) and anhydrous 1-propanol (purity>99.9%) were purchased from Fisher Scientific (Pittsburgh, Pa.) and were of the highest grade commercially available. The solvents were stored over oven-dried 3 Å molecular sieves (4-8 mesh beads, Fisher Scientific) for at least 24 h prior to use. The enzyme preparations were prepared and stored in 15 mL flat-bottom glass vials that were closed with Teflon-lined screw caps after lyophilization. Activity assays were performed in 15 mL Teflon screw capped round bottom test tubes. All glassware was low-extractable borosilicate glass (Fisher-Scientific).

Analytical

In order to determine the amount of the enzymatically synthesized N-acetyl-L-phenylalanine propyl ester (APPE), 400 µL aliquots of the homogeneous reaction mixtures were taken and spun at 3300 rpm for 30 seconds in Eppendorf tubes using a microcentrifuge. The supernatant was then analyzed via gas chromatography (GC, 1 µL sample, Varian Model 3800, Varian Analytical Instruments, Sugar Land, Tex.; DB-5 capillary column, 30 m length, 0.25 mm I.D., 0.25 µm film thickness; J&W Scientific Inc., Folsom, Calif., helium carrier gas flow 1.3 mL/min, split ratio 1/400, injection and detection at 250° C., linear column temperature ramp 150-210° C. at 8° C./min). The water content of organic solutions (2 mL sample size) was measured by coulometric Karl Fischer titration (Denver Model 275KF titration module, Model 270 controller, Denver Instrument, Denver, Colo.). Hydranal Water Standard 0.10 (Riedel-de Haën, 100 mg water/g) was used to check the accuracy and reproducibility of the Karl Fischer titration.

Procedure to Prepare Enzyme Preparations

Enzyme masses were determined by weighing the as-received enzyme. SC was diluted by shaking in a 10 mM potassium phosphate buffer at pH 7.8 (at room temperature) so that enzyme concentrations of 0.1 mg/mL to 6.67 mg/mL were achieved. As-received fumed silica was added to reach 0 to 98.5 wt % of silica relative to the final enzyme preparation mass. The aqueous preparations were sonicated for 10 minutes in a water bath to form homogeneous suspensions. A 3 mL aliquot per sample was then frozen in a 15 mL glass vial by immersing in liquid nitrogen for 20 minutes. This step was later replaced by placing the sample in a refrigerator at −20° C. (see below). The enzyme preparations were lyophilized for 72 h (48 h of primary drying, 24 h of secondary drying, VirTis model 10-MR-TR; Gardiner, N.Y.) at a condenser temperature of −50° C. and a shelf temperature of 25° C. The preparations were stored in screw capped glass vials at −20° C.

Kinetic Measurements

The kinetic constants $v_{max}$ and $K_m$ for the enzyme preparations were determined in nearly anhydrous hexane containing 8.3+/−3.1 ppm (w/w) H$_2$O as determined by Karl-Fischer titration. The method for enzyme activation by adding inorganic salts prior to lyophilization (Ru et al.) was reproduced for reference. Our data and the data from Ru, et al. are shown in Table 1 for comparison.

TABLE 1

Effect of 98.5 wt % fumed silica and 98.5 wt % Aeroxide ® Alu C alumina as an additive during lyophilization of SC (preparations pre-frozen in liquid nitrogen (LN$_2$) or shelf-frozen at −20° C. as indicated) compared with KCl activation data from Ru, et al., and an additive free preparation.

| Additive | $v_{max}$ (µmol$_{APEE}$ min$^{-1}$ mg$^{-1}_{enz}$) | $K_m$ (mM) | catalytic efficiency $v_{max}/K_m$ (µmol$_{APEE}$ min$^{-1}$ mg$^{-1}_{enz}$ mM) |
|---|---|---|---|
| 98.5 wt % fumed silica (preparation pre-frozen LN$_2$) | 341.7 | 9.5 | 35.9 |
| 98.5 wt % fumed silica (preparation pre-frozen at −20° C.) | 317.9 | 3.3 | 96.8 |
| 98.5 wt % Aeroxide ® Alu C (preparation pre-frozen in LN$_2$) | 559.2 | 10.2 | 54.9 |
| 98 wt % KCl our data, method see Ru, et al. | 122 | 2.2 | 56.5 |
| 98 wt % KCl, Ru, et al. | 175 | 7.0 | 24.9 |
| none, enzyme only | 2.6 | 9.1 | 0.28 |

The model reaction was the transesterification reaction of N-acetyl-L-phenylalanine ethyl ester (APEE) with 1-propanol. This reaction was carried out as reported by Ru, et al. Briefly, 5 mg of activated enzyme preparation were added to 5 mL of hexane containing 5-40 mM APEE, 0.85 M 1-propanol and 1.5 mM nonadecane as a non-reacting internal standard for GC analysis. The transesterification was carried out in 15 mL Teflon-lined screw capped glass vials constantly shaken in an incubator at 30° C. Initial rate measurements were carried out over a period of 30-75 minutes for additive-containing enzyme preparations (fumed silica or salt) and due to lower reaction rates for 90-270 minutes for additive free lyophilized SC. Initial rates were determined from linear fits over the average values of the GC measurements taken in duplicate. Kinetic parameters were calculated by fitting the obtained initial rate data to the Michaelis-Menten equation using Lineweaver-Burk plots.

FIG. 1 shows the good linearity of the Lineweaver-Burk plot for the model reaction (above) catalyzed by our SC preparation with 98.5 wt % fumed silica. The reference experiment where no enzyme was added, but the fumed silica was included and processed identically to the enzyme activation experiments showed no measurable catalytic activity.

The final water content of the supernatant (spun for about 2 minutes at 3300 rpm in a centrifuge) after completing the assay was determined by Karl Fischer titration to range between 257 ppm and 318 ppm (w/w) depending on the added substrate concentration. This increase in water content compared to the initial water content in hexane is mainly due to the addition of water with the 1-propanol and the enzyme preparation.

Figure 2:
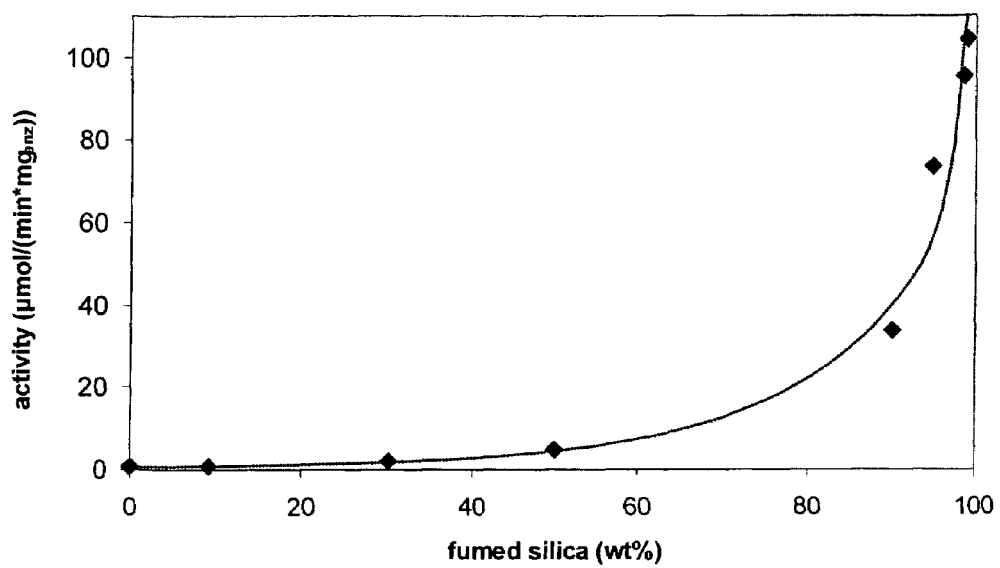
FIG. 2 is a graph of catalytic activity vs. fumed silica content for SC preparations containing various amounts of fumed silica.

FIG. 2 shows the enormous enhancement of the transesterification activity (represented by the initial reaction rate) of lyophilized SC in hexane as a function of the fumed silica content of the catalyst preparation. A sharp increase in activity was observed as the fumed silica content reaches up to 98.5 wt %. This strong activity increase at high relative amounts of additive (salt or, in our case, fumed silica) relative to the mass of preparation is similar to results for inorganic salts.

Figure 3:
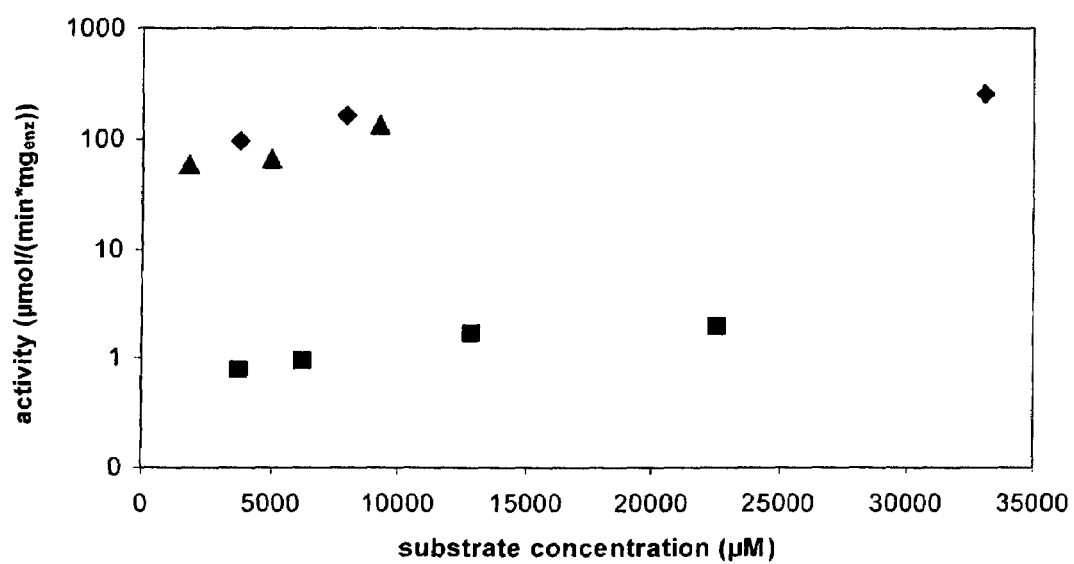
FIG. 3 is a graph of catalytic activity vs. substrate concentration for an enzyme-only SC preparation (■), an SC preparation containing 98 wt. % KCl (▲), and an SC preparation containing 98.5 wt. % fumed silica (♦), in nearly anhydrous hexane at different APEE concentrations.

FIG. 3 shows the effect that the addition of 98.5 wt % fumed silica has on the initial reaction rates at different substrate concentrations compared to a SC preparation containing 98 wt % KCl and an additive free one (enzyme-only, lyophilized). Table 1 shows that the observed maximum velocity $v_{max}$ as well as the catalytic efficiency $v_{max}/K_m$ (the activity of the catalyst at limiting substrate concentrations) for the 98.5 wt % fumed silica containing preparation (pre-frozen in $LN_2$) was about 130 fold higher when comparing to enzyme only. Compared to KCl-activation the $v_{max}$ is still twice as high whereas the catalytic efficiency shows an increase of about 1.5 fold over salt activation. While the value of $K_m$ stayed nearly constant the increase in catalytic efficiency appeared mainly due to the enhanced maximum velocity. Also shown in Table 1 is an experiment where the $LN_2$ pre-freezing step was replaced for the fumed silica activation procedure by simple shelf-freezing in a refrigerator at $-20°$ C. The results show that the efficiency can be further increased due to the lowered $K_m$ whereas $v_{max}$ remained nearly constant.

While SC with an isoelectric point of pH 9.8 possesses a positive net surface charge in the buffer (pH 7.8) from which it was lyophilized, fumed silica has a negative surface charge at this pH. This surface charge likely aids in non-covalent immobilization.

Figure 4A:
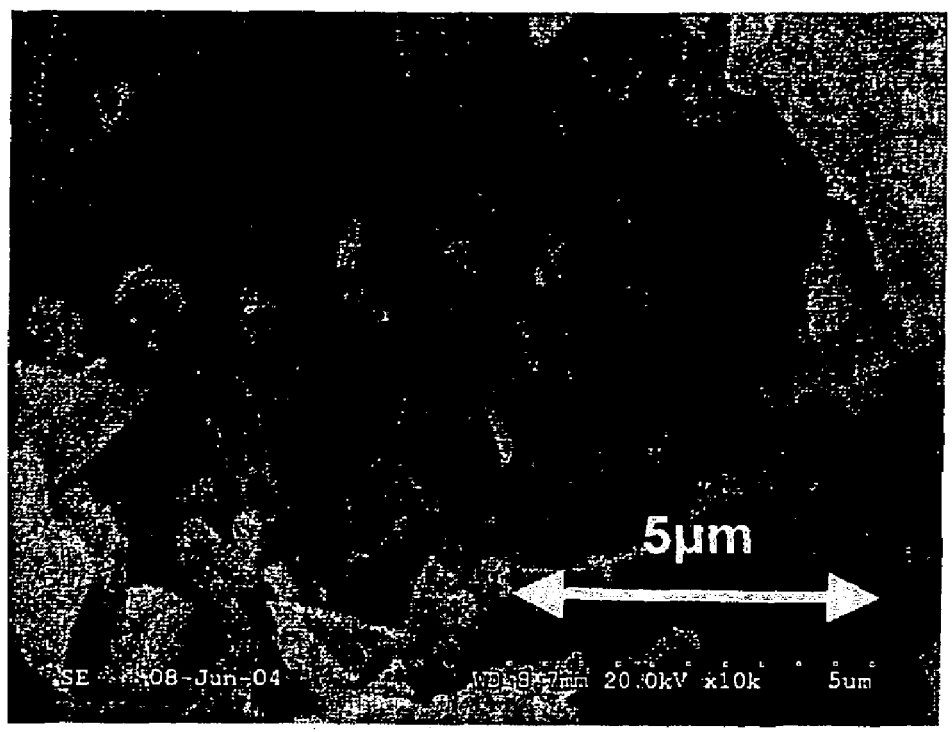
FIG. 4A is a scanning electron micrograph (SEM) of lyophilized SC without support.

The presence of fumed silica or KCl influences the physical result of lyophilization. FIG. 3A shows a scanning electron micrograph (SEM) of SC which has been lyophilized in the absence of FS or KCl. FIG. 3A can be compared to environmental SEM pictures for lyophilized subtilisin (K. Roziewski, A. J. Russell, *Biotechnol. Bioeng.* 39 (1992)). The structures shown in Roziewski, et al. illustrate some resemblance to the sheet-like structures of the present invention (FIG. 4A). A direct comparison may be complicated by possible differences in the lyophilization procedure.

After the lyophilization process the additive-free enzyme is present in the form of sheets, some of which have thicknesses on the order of micrometers. If this preparation were used in water the sheets would likely dissolve allowing each enzyme molecule to catalyze the desired reaction. Yet, when used in hexane, the enzyme will not dissolve. In hexane the enzyme molecules in the interior of the sheets seen in FIG. 4A are believed to be essentially useless for catalysis.

Figure 4B:
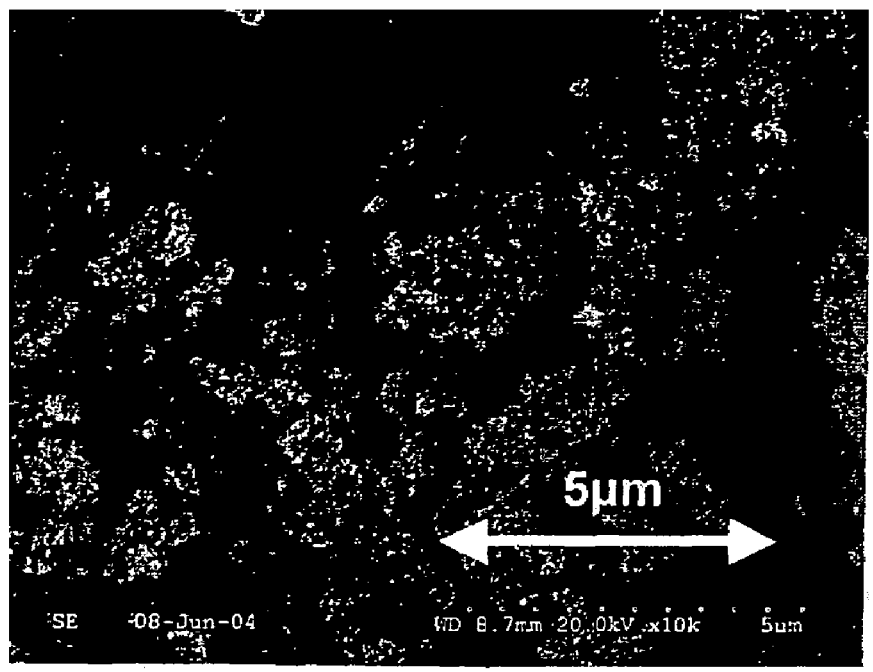
FIG. 4B is an SEM of 98 wt. % fumed silica added to an aqueous buffer solution of enzyme prior to lyophilization.

In contrast, when the lyophilization takes place in presence of a significant amount of FS, the resulting particles are much smaller. As shown in FIG. 4B, the particle sizes are now on the order of 1/100th of a micrometer or smaller. This is consistent with the size of individual primary FS particles (native diameter about 7-50 nanometers). It is believed that the resulting preparation consists of non-porous FS particles with enzyme deposited on the surface. The thickness of the enzyme layer is dependent on the ratio of mass of enzyme to the available surface area of FS.

Figure 4C:
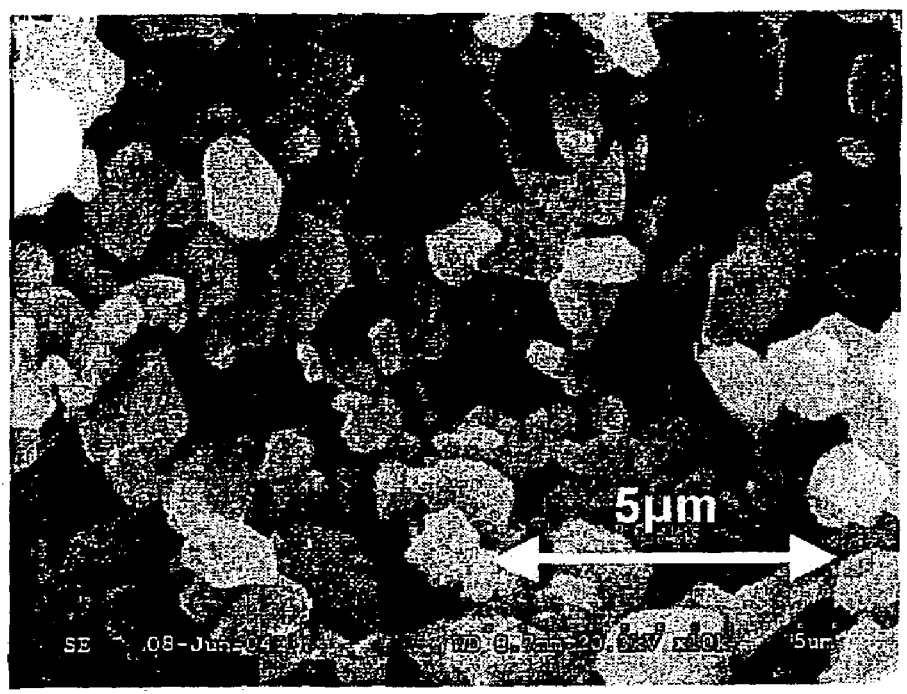
FIG. 4C is an SEM of 98 wt. % KCl added to an aqueous buffer solution of enzyme prior to lyophilization (liquid nitrogen pre-freezing)

For comparison, an image of enzyme lyophilized in the presence of KCl is shown in FIG. 4C. Salt crystals of submicrometer dimensions are evident. The differences in the geometry and specific surface area (surface area per mass) of salt crystals and FS may play an important role in determining the apparent catalytic activity per mass of enzyme.

Mass transfer limitations are believed to be the major obstacle to high activity of the pure SC in hexane. If this is true, any preparation procedure that produces well dispersed enzymes in hexane will have a higher activity than the enzyme alone.

Figure 5:
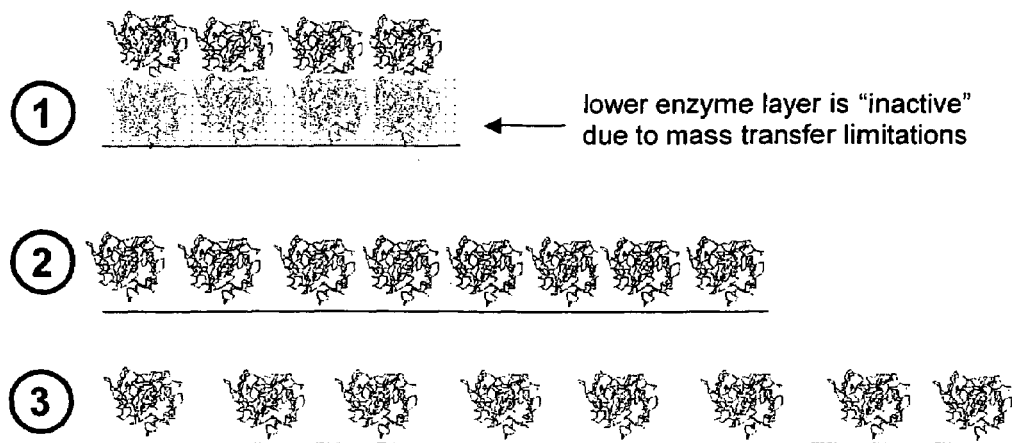
FIG. 5 is a schematic representation of three possible stages (multilayer, monolayer, thinned-out monolayer) of enzyme adsorption to the surface of fumed silica.

FIG. 5 shows schematically how enzyme molecules may interact with the fumed silica surface. It is postulated that only enzyme molecules that are directly exposed to solution contribute significantly to the enzyme activity that is detected. This assumption is supported by the very low activity of pure lyophilized enzyme in hexane, where thick sheets of enzyme only allow few enzyme molecules to have relatively unimpeded access to substrate. FIG. 5 shows schematically why one observes increased enzyme activity (per mass of enzyme) as more and more FS area is made available for immobilization of the enzyme. As seen in this Figure, when a large ratio of enzyme to non-porous substrate (FS) is employed, the enzyme is deposited in multiple layers. Only the uppermost layer is freely accessible for catalysis. As the ratio of non-porous substrate to enzyme is increased the thickness of the enzyme layer is reduced until it reaches the monolayer level. Upon further increase in the support-to-enzyme ratio a sub-monolayer coverage is reached with individual enzyme molecules highly dispersed and available for catalysis. We shall first calculate significant parameters and then examine experimental evidence to support this view.

According to this model the catalytic activity of an enzyme preparation (enzyme immobilized on support) should increase when the relative amount of enzyme per available surface area is increased. When a monolayer of enzyme on the carrier surface has been reached further addition of enzyme to the preparation may result in no significant further increase of activity of the preparation. For fumed silica the specific surface area $F_{spec(FS)}$ was given by the supplier as 258 $m^2/g_{FS}$. The number $n_{SC}$ of Subtilisin Carlsberg molecules needed to form a complete monolayer on the surface of fumed silica can be estimated using the area $f_{SC}$ that one molecule of SC requires on the surface of FS (eq. 1). The following calculation assumes the area required for adsorption of an individual SC molecule to be approximately $f_{SC}=20$ $nm^2$. This estimate is based on a correlation of molecular weight and radius with added area to account for packing of "hard" spherical molecules on a plane.

$$n_{SC}=F_{spec(FS)}/f_{SC}\approx 1.3\times 10^{10}/g_{FS}$$

Figure 6:
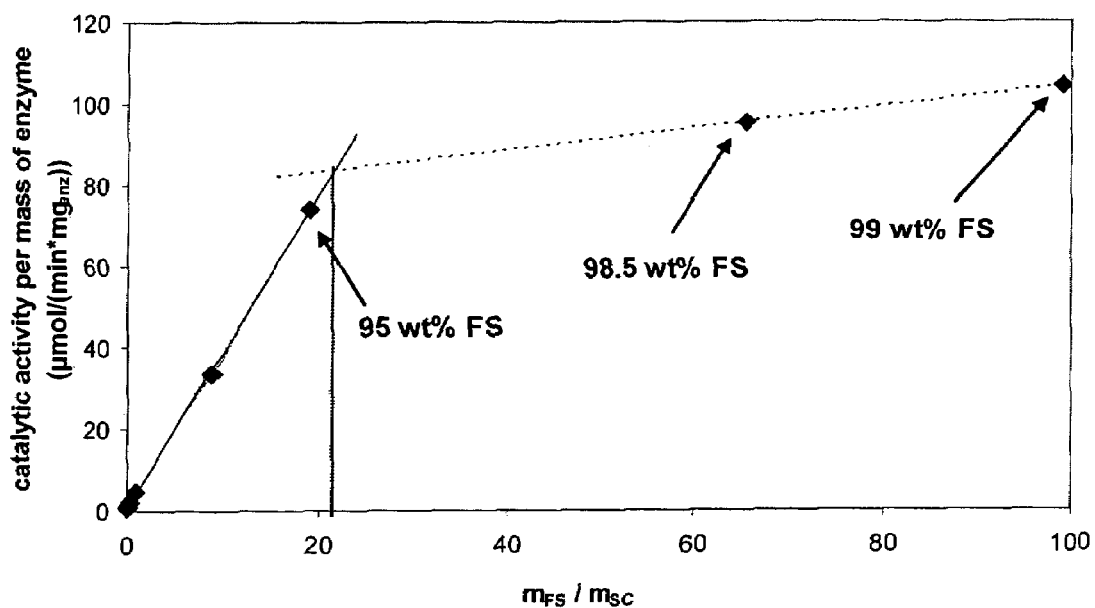
FIG. 6 is a graph of catalytic activity/mass of enzyme vs. mass of fumed silica/mass of SC as described in Example 1.

The ratio of the mass of FS $m_{FS}$ to the mass of subtilisin Carlsberg $m_{SC}$ needed to form a dense monolayer on the surface of fumed silica is then $$m_{FS}/m_{FC}=m_{FS}/MW_{SC}/N_{Av}n_{SC}m_{FS}\approx 1.72\ g_{FS}/g_{SC}$$

where $N_{Av}$ is Avogadro's constant and $MW_{SC}$ is the molar mass of SC which was assumed to be 27000 g/mol. FIG. 6 shows that the experimentally determined catalytic activities for SC preparations still increase far above the estimated monolayer value of $m_{FS}/m_{SC}$ of 1.72. Reasons may include that the surface area of FS actually available for enzyme immobilization is less than the area reported by the manufacturer, and that the optimum monolayer packing density for fully accessible and active enzyme molecules may be less than the perfect coverage assumed above. We hypothesize that the intersection of the trend lines in FIG. 5 ($m_{FS}/m_{SC}\sim 23$) indicates where a further increase of the relative amount of mass (or available area) of FS available to the enzyme does not contribute strongly to increase enzymatic activity since the available area is already nearly sufficient for all enzyme molecules to be easily accessible to the solution.

These results can be checked against the specific catalytic activities (catalytic activity normalized by mass of final enzyme preparation) in hexane for the different enzyme preparations. Since an increase in the amount of FS in the preparation is only effective (in respect to the catalytic activity) until every enzyme molecule is finally accessible, a maximum should occur at about 96 wt % FS according to the considerations above (FIG. 5). The enzyme preparation containing 95 wt % FS shows the highest specific catalytic activity. Substrate conversions after 60 min for the different FS containing enzyme preparations at an initial substrate concentration of 5 mM also reach the maximum of 25.0% at 95 wt % FS.

The inorganic hydrophilic material (Aeroxide® Alu C) was employed to investigate if material-specific effects could be detected for the observed activation. Aeroxide® Alu C is a highly dispersed fumed aluminum oxide with a nominal specific surface area of 100+/−15 m$^2$/g (about ½ the value of FS). The enzyme preparation was prepared as described above for fumed silica. A final weight ratio of Aeroxide® Alu C of 98.5% with pre-freezing for 20 min in LN$_2$ was prepared. Since $K_m$ remained nearly constant when compared to the equivalent FS preparation (Table 1), the 1.5 fold increase in catalytic efficiency can be ascribed to the increase in $v_{max}$ of about 60%. This further supports the theory that the activation of enzymes in organic media is due mainly to improved mass transfer and is largely independent of the support material.

Finally, the results using KCl and reported in Table 1 are consistent with the surface area hypothesis. Ru et al. have suggested that the enhanced activity for the enzyme/salt preparations is mainly the result of subtle interactions between salt and enzyme prior to and after lyophilization. While these interactions may contribute to the properties of salt-containing preparations, the simpler explanation of reduced mass transfer limitations by dispersing the enzyme molecules on a surface at or below monolayer coverage appears to be the dominant effect.

It was reported by Ru et al. that the salt activation method showed the best results when the mixtures were pre-frozen most rapidly in LN$_2$. It is well known that more rapid cooling of solutions of inorganic salts will generally produce smaller salt crystals. The results for LN$_2$ pre-freezing of salt-containing enzyme solutions therefore seem to support our hypothesis that an increased surface area available for enzyme immobilization is to a large part responsible for increased enzyme activity.

This example demonstrates that SC can be highly activated in organic solvents by lyophilization in the presence of fumed silica and fumed aluminum oxide. The activation reaches and sometimes exceeds that reported using inorganic salts as additives before lyophilization. The amount of fumed silica needed can be related to the surface area needed for formation of an enzyme monolayer. Once enzyme multilayers are formed any additional enzyme appears not well utilized for catalysis. This shows that mass transfer limitations are one main obstacle to the efficient use of enzymes in organic solvents. Specific interactions of soluble salts with enzymes are not needed to produce activated SC preparations for use in hexane. The availability of easily produced and inexpensive highly active enzyme preparations for use in organic solvents may advance applications such as the production of specialty polymers and optically active specialty chemicals and pharmaceuticals.

Example 2

In this example, the novel activated enzyme products of the invention were used in a packed bed reactor, and important reactor parameters were measured.

Materials

Subtilisin Carlsberg (SC, EC 3.4.21.14; proteinase from *Bacillus licheniformis*; specific activity of 8 units/mg solid), fumed silica (purity 99.8%, specific surface area 258 m$^2$/g, particle diameter 7-50 nanometer, manufacturer's data), and nonadecane (puriss. p.a., internal standard for gas chromatography) were obtained from Sigma-Aldrich (St. Louis, Mo.). Fumed silica consists of chain-like entangled agglomerates of solid primary silica particles with a few nanometers diameter. N-acetyl-L-phenylalanine ethyl ester (APEE, purity>99%) was obtained from Bachem California Inc. (Torrance, Calif.). KH$_2$PO$_4$ (purity>99%), hexane (optima grade, purity>99.9%) and anhydrous 1-propanol (purity>99.9%) were from Fisher Scientific (Pittsburgh, Pa.) and were of the highest grade commercially available. The solvents were stored over 3 Å molecular sieves (4-8 mesh beads, Fisher Scientific) for at least 24 h prior to use. The enzyme preparations were prepared and stored at −20° C. in 15 mL flat-bottom glass vials closed with Teflon-lined screw caps after lyophilization. Batch activity assays were performed in 15 mL Teflon screw capped round bottom test tubes. All glassware was low-extractable borosilicate glass (Fisher Scientific).

Analytical

To determine the amount of the enzymatically synthesized N-acetyl-L-phenylalanine propyl ester (APPE), 400 μL aliquots of the effluent from the packed bed reactors were analyzed via gas chromatography (GC, 1 μL sample, Varian Model 3800, Varian Analytical Instruments, Sugar Land, Tex.; DB-5 capillary column, 30 m, 0.25 mm I.D., 0.25 μm film thickness; J&W Scientific Inc., Folsom, Calif.; helium carrier gas 1.3 mL/min, 1/400 split, injection/detection at 250° C., linear column temperature ramp 150-210° C. at 8° C./min; alternatively a Hewlett Packard HP6890 gas chromatograph with similar parameters was used). The analytical procedures of Analytical and experimental procedures and materials for batch reactions were described in Example 1.

Fumed Silica/Enzyme Preparations

The preparations were prepared as set forth in Example 1. The 95 wt. % fumed silica-enzyme preparations were used in the packed columns.

Column Packing and Operation

Figure 7:
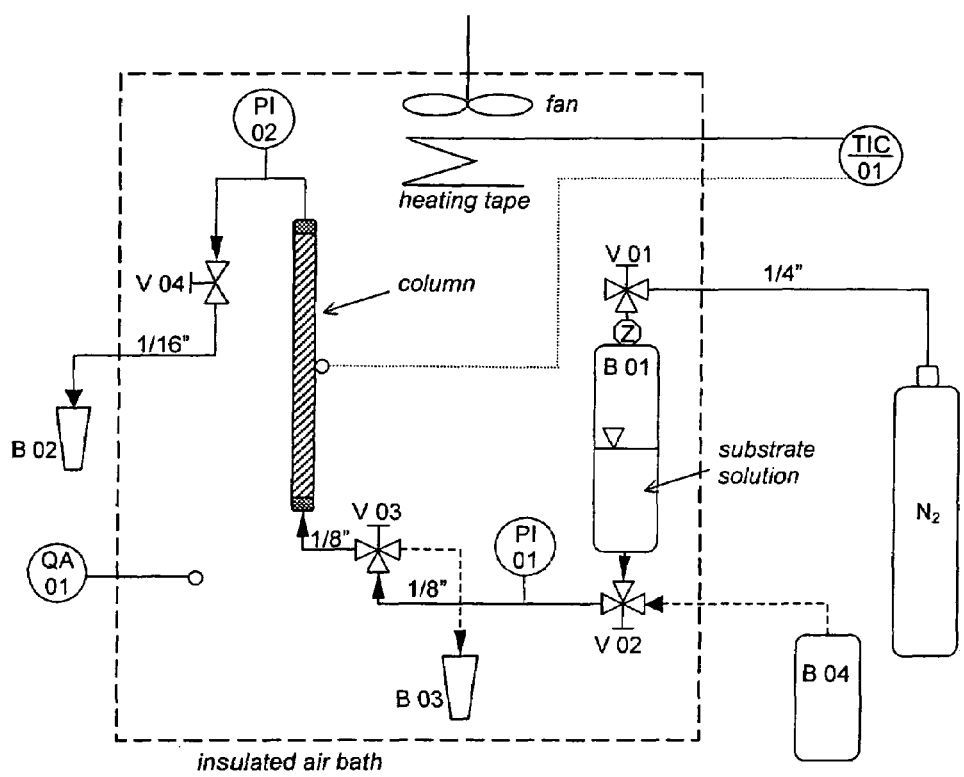
FIG. 7 is a schematic representation of the test setup used in Example 2 for the packed bed transesterification catalysis by SC/FS preparations, where the column, all tubing and valves, and reservoir B01 were formed of stainless steel, and all samples were taken at B02 and B03, and wherein B04 is a wash bottle containing the substrate solution loaded into B01 and QA01 is a combustible gas detector used to monitor hexane leaks.

The packed bed reactors were always operated in a temperature controlled air bath (FIG. 7, 30+/−0.2° C.) with a 300 ml sample bomb as reactant reservoir. The hydrostatic pressure to force liquid through the bed was provided by compressed nitrogen (Linweld, Manhattan, Kans.). The nitrogen pressure was set between 30 and 180 psi depending on the bed height and the flow rate of the reactant solution (0.27-2.05 mL/min).

Figure 8:
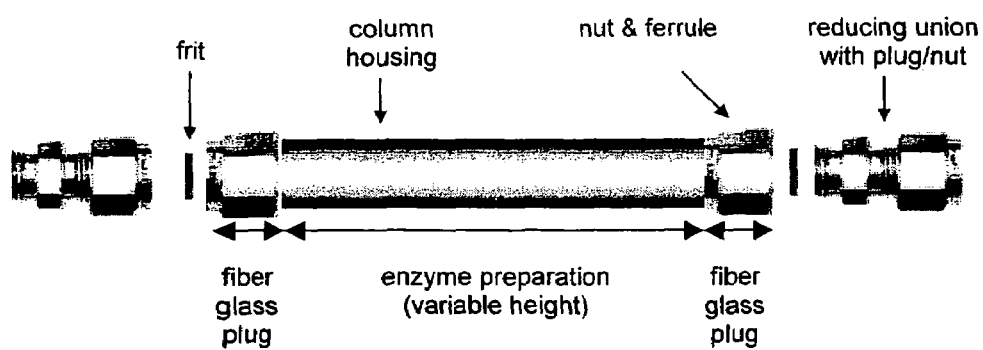
FIG. 8 is a schematic representation of the packed column used in the FIG. 7 setup.

The enzyme/fumed silica preparations appeared as a free-flowing white powder after lyophilization. Sections of ¼" stainless steel tubing (ID=4.6 mm; packed bed lengths 29-220 mm) were used as housings for the packed beds (FIG. 8). The beds were packed by manual compaction of the enzyme preparation using a stainless steel rod (OD=4.5 mm) onto a glass wool plug resting on a metal frit installed at one end of the stainless steel tubing section. Another glass wool plug and frit was then used to close the column. Consistent superficial densities of the packed beds of 0.22 mg enzyme preparation/mm$^3$ for all bed heights indicated that the packing procedure was reproducible. The bed void volume was about 90% based on the mass of enzyme preparation, overall volume of the bed, and the bulk density of silica, neglecting the volume occupied by the enzyme. The packed columns were rinsed with hexane and stored capped and filled with hexane at −20° C.

Two different batches of enzyme preparation were used in the columns. The data in FIG. 9 was obtained with one enzyme preparation batch (A), while the data in FIG. 10 and FIG. 11 were obtained with a second batch (B) prepared independently.

The substrate concentration was always $[S]_0$=36.31 mM APEE in the hexane fed to the beds. The flow rate through the beds was determined volumetrically within less then 2% of the reported value. Steady state was assumed after about twice the average residence time of feed solution in the packed bed had elapsed.

This example confirms that the enzyme preparations of the invention can be used in packed bed reactors. Plug flow with negligible axial dispersion can be safely assumed in this experiment. The Michaelis-Menten parameters $K_m$ and $V_{max}$ for the catalyst preparation used here (95 wt % FS/5 wt % SC), were determined in batch reactions where external mass transfer was assumed negligible and found to be $K_m$=14.6 mM and $V_{max}$=116.4 µmol/min $mg_{enz}$. These values can only be matched in packed bed reactors when mass transfer limitations are negligible. To determine when mass transfer limitations become negligible one can increase the flow rate through the packed bed in steps and observe the rate of reaction achieved. The performance of the batch reactions should be approached at high flowrates in the packed bed reactor.

The packed beds were operated at 36.31 mM substrate concentration [S] in the feed which substantially exceeds the $K_m$ value derived from batch experiments. If the conversion in a single pass through the bed is not excessive then zero-order reaction in [S] can be assumed and the packed bed performance should approach the batch reaction data.

Determination of Mass Transfer Limits

Figure 9:
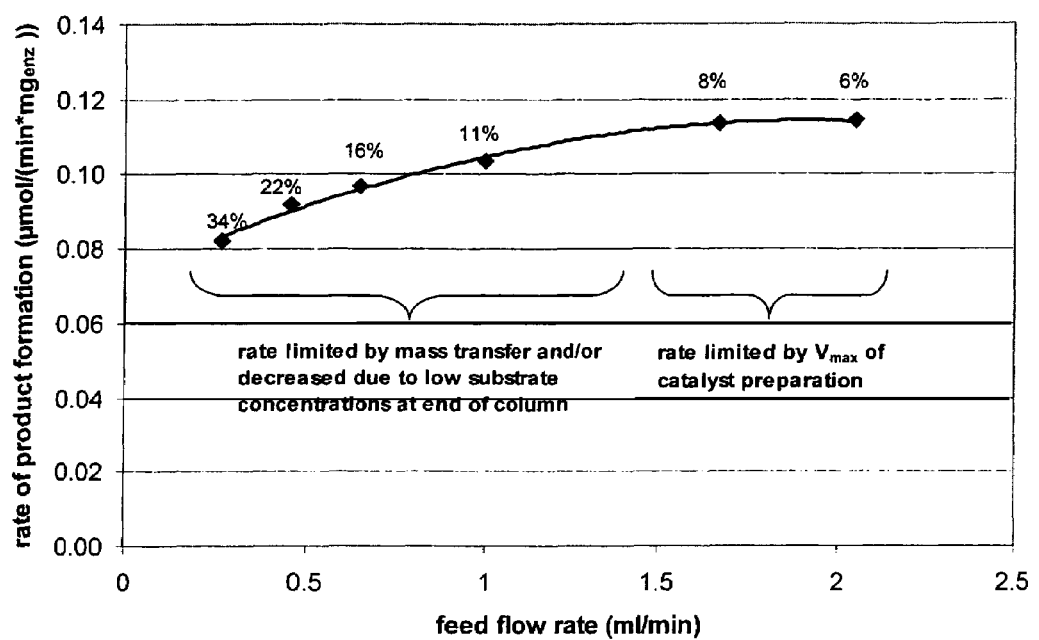
FIG. 9 is a graph of product formation rate vs. feed flow rate for the packed bed transesterification reactions of Example 2.

The primary fumed silica particles are essentially non-porous so that external mass transfer in the hydrodynamic boundary layers around the particles and particle agglomerates but not diffusion limitations in the particles is of concern. Since the reaction rate v with which substrate is converted into product is strongly dependent on the actual substrate concentration that is available to the enzyme, the stagnant boundary layer between bulk solution and the silica surfaces where the enzyme resides should be minimized. This minimizes diffusional limitations that can lead to low apparent reaction rates. Conversions were calculated by analyzing the effluent from the bed at some time t (at steady state conditions) for the substrate concentration $[S]_t$ and calculating the conversion according to %conversion=$([S]_0-[S]_t/[S]_0) \times 100$ FIG. 9 shows the steady-state conversions and the rates of product formation at different feed flow rates for a packed bed (bed height h=220 mm, diameter 4.6 mm, enzyme preparation mass 0.8018 g). A feed flow rate above about 1.4 ml/min appears sufficient to avoid mass transfer limitations since no significant further increase of the rate of product formation with increased flow rate is observed. The conversion had decreased to near 7% when mass transfer limitations became negligible. At this relatively low conversion the reaction will be assumed to take place with $V_{max}$ (zero order) essentially over the whole length of the packed bed since the rate of product formation approaches the maximum of about 0.114 µmol/(min $mg_{enz}$).

Mass transfer limitations can be excluded at flow rates above about 1.4 ml/min, similar to other results reported. All further reactions were performed at flow rates above 1.4 ml/min to investigate the behavior of the enzyme preparation with negligible mass transfer limitations.

Influence of Catalyst Bed Height on Substrate Conversion

Figure 10:
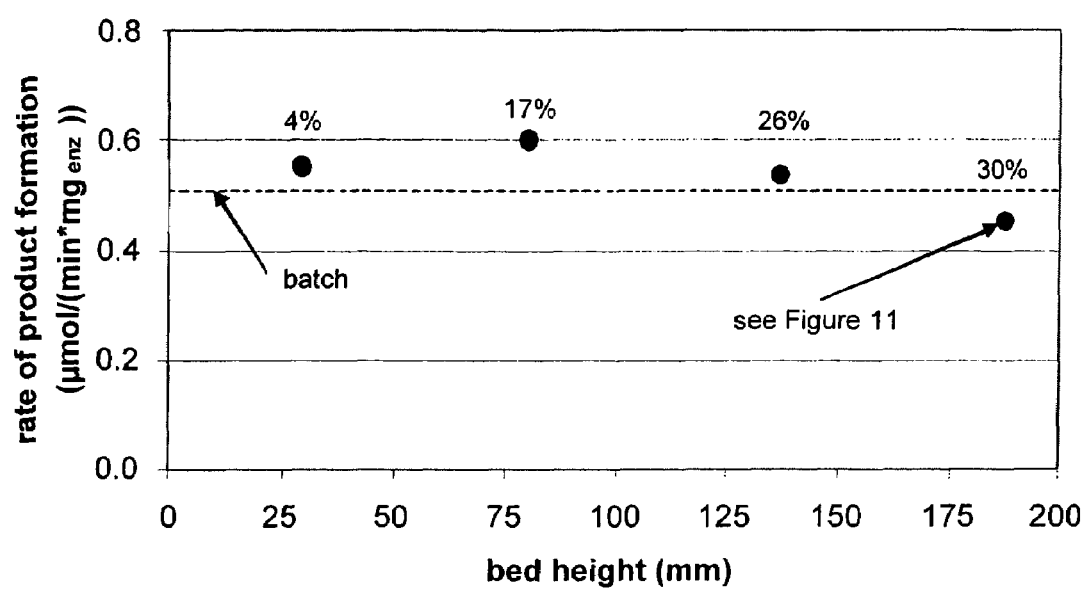
FIG. 10 is a graph of product formation rate vs. feed flow rate for the packed bed transesterification reactions of Example 2, for different bed heights.

The steady-state conversions and the rates of product formation for different packed bed heights at a constant feed flow rate of 1.44 ml/min are shown in FIG. 10. All data in FIG. 10 and FIG. 11 were obtained using the same batch A of enzyme preparation. This batch A was prepared independently from the enzyme preparation used for FIG. 9 (Batch B). Data from FIG. 9 should therefore only be use for qualitative comparison with the data in FIGS. 10 and 11. However, since the rate of product formation is lower for the batch B used for FIGS. 10 and 11 than the preparation batch A used in FIG. 9, the assumption of absence of mass transfer limitations is still valid.

The relatively constant substrate conversion over the whole length of the columns confirms that the reaction is zero-order. The rate for a packed bed height of 188 mm decreases somewhat to about 0.43 µmol/(min $mg_{enz}$) when compared to the average value of the three other bed heights. This may be due to typical issues with small-scale packed beds like bypassing or channeling in the bed, non-uniform packing, bed compression etc. A linear regression ($R^2$=0.97) gives an average conversion of 0.17% per mm packed bed depth.

Operational Stability of Packed Bed Reactor over Period of 6 Hours

Figure 11:
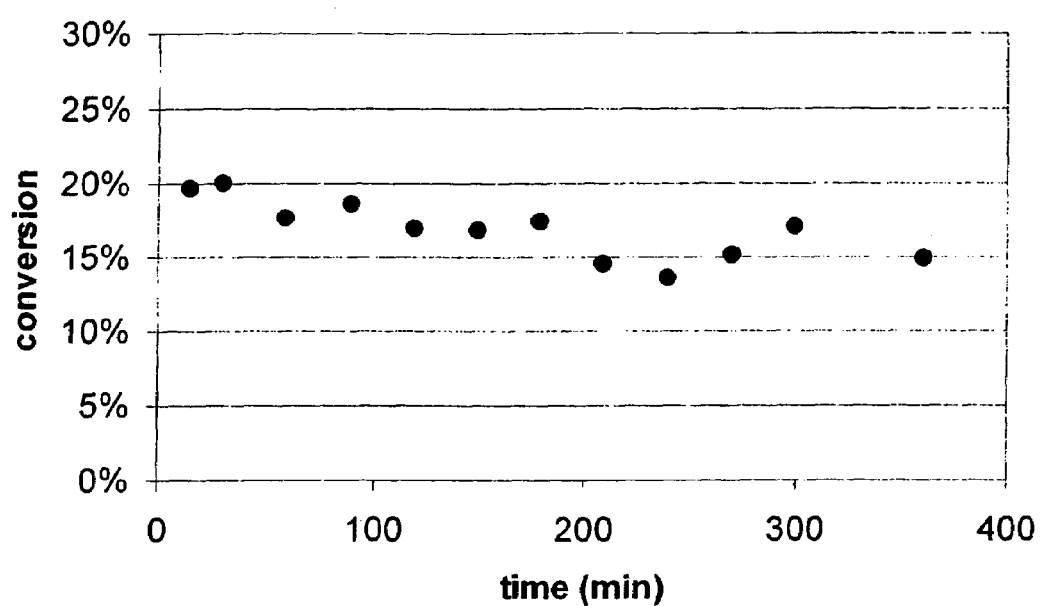
FIG. 11 is a graph of percent conversion vs. time for the packed bed transesterification reactions of Example 2, after storage under hexane for 15 days at −20° C. (188 mm bed height, feed flow rate 1.3+/−0.02 ml/min.).

The operational stability of the packed bed reactor using the column with a bed height of 188 mm (see FIG. 4) was studied during 6 hours of continuous operation with a feed containing 36.31 mM APEE in hexane (30+/−0.2° C.; 1.3+/−0.02 mL/min). The column had been rinsed with pure dry hexane (stored over 3 Å mol. sieves for at least 24 hours), closed and stored at −20° C. for 15 days. The previous tests reported in FIGS. 10 and 11 showed that the conversion decreased about 41%, compared to before-storage testing where a conversion of 30% was observed. There is also a slight downward trend from about 20% to 15% conversion (FIG. 11) during this test. This loss in conversion is comparable to literature results. The reasons could be compression of the catalyst bed causing less favorable flow conditions, or loss of enzyme activity. Nonetheless, substantial activity remained after prolonged storage.

Example 3

This Example confirms that lyophilization of the initial enzyme/support mixture is not required, although lyophilization is preferred.

Enzyme Solution Preparation

Generally, the procedure follows that of Example 1. A solution consisting of 5 mg of subtilisin Carlsberg as received, 4.4 mL of 10 mM $KH_2PO_4$, and 0.33 g of >99.8% purity fumed silica was prepared. The final solution consisted of 98.5 wt % (relative to absolute weight of the final preparation). 1 M $KOH_{aq}$ was added to adjust the pH to 8.2, the pH found by Wuerges to provide optimum activity was 7.8.

Sonification and Drying the Enzyme

The enzyme solution described above was placed in a closed glass container and then sonicated for 25 minutes, in order to prevent clumping and to promote dispersion of the enzyme silica mixture. The enzyme solution appeared as a hazy white cloud with no large clumps. After sonication the solution was inserted into a 300 mL polypropylene wash bottle and dried for 30 min at room temperature and near atmospheric pressure using 98% pure compressed nitrogen from a pressurized nitrogen cylinder. Tubing connected to the pressurized nitrogen cylinder (delivery pressure 5 psig at the cylinder pressure gauge) was inserted in a hole in the sidewall of the bottle and the lid was left cracked to allow gas to exit. The enzyme solution was dried to constant weight. A white powder remained.

A control experiment was performed using the fumed silica and buffer, but omitting the enzyme. The control solution was sonicated and dried as described above to determine the effect of the enzyme on the process. The product retained the same appearance through out the drying process.

Reaction the Enzyme with APEE

The same model reaction as described in Example 1 was performed.

The hexane and 1-propanol were dried by placing each in a container with activated 3 Å molecular sieves for 24 hours. A 5 mL sample of hexane containing 0.85 M 1-propanol and 1.5 mM nonadecane was used to carry out the reaction. The nonadecane provided a non-reacting internal standard to aid in gas chromatography analysis. The concentration of APEE was 36.5 mM. The enzyme, APEE, and hexane solutions were placed in a centrifuge tube. The test tube was then shaken constantly using a Mini Vortex and kept at a temperature of 30° C.

Testing of the Enzyme Solution

The enzymatic activity was determined by monitoring the amount of APPE formed over a 75 min period using a gas chromatograph. Samples of 400 µl were extracted from the batch reaction at times of 0, 15, 30, 45, 60, and 75 min. The samples were then centrifuged for 30 seconds using a microcentrifuge at 3300 rpm. Then, 1 µl samples from the supernatant were injected into the gas chromatograph.

Results

Analysis of the transesterification reaction confirmed that the SC/FS product of this Example had a catalytic effect. However, the effect was less pronounced than with the lyophilized products of Example 1.

We claim:

1. An enzyme preparation comprising a support of nanoscale size solid, water insoluble, inorganic oxide support particles with hydrophilic surfaces and having a diameter of from about 0.1-100 nm and a surface area of from about 150-500 $m_2/g$, with enzyme molecules electrostatically adhered to the hydrophilic surfaces of said particles with up to about 70% of the total surface area of said particles covered by said enzyme molecules, said preparation prepared by mixing said particles with said enzyme molecules in an aqueous system under pH conditions establishing opposite charges for the particles and the enzyme molecules, respectively, and electrostatically adhering the enzyme molecules to the particles to form enzyme-coated particles, and thereafter removing virtually all of the water from the enzyme-coated particles, said water removal step selected from the group consisting of lyophilization of the enzyme-coated particles and passing a drying gas over the enzyme-coated particles.

2. The preparation of claim 1, said solid support particles having a diameter of from about 5-50 nm.

3. The preparation of claim 1, said solid support particles being aggregated to form bodies prior to said electrostatic adherence of said enzyme molecules.

4. The preparation of claim 3, said aggregated bodies having a length of from about 100-1000 nm.

5. The preparation of claim 1, said enzyme selected from the group consisting of catalytic antibodies, oxidases, oxidoreductases, transferases, lyases, isomerases, ligases, hydrolases with acyl transferase activity in organic solvents, peroxidases, tyrosinases, dehydrogenases, lipases, proteases, nucleases, aldolases, phosphatases, sulfatases, chymotripsins, tannases, subtilisins, papain, pepsin, thermolysin, thrombin and mixtures thereof.

6. The preparation of claim 1, said solid support particles selected from the group consisting of fumed silica and fumed alumina.

7. In a method of conducting a reaction in organic solvent wherein an enzyme catalyzes a reaction between a plurality of reactants to obtain reaction product, the improvement which comprises using the preparation of claim 1 as a catalyst in the reaction.

* * * * *